(12) United States Patent
Vayser et al.

(10) Patent No.: US 7,510,524 B2
(45) Date of Patent: Mar. 31, 2009

(54) OPTICAL WAVEGUIDE SHEATH

(75) Inventors: Alex Vayser, Mission Viejo, CA (US); Kenneth Trauner, San Francisco, CA (US); Jon Gasson, San Francisco, CA (US); Tom Grey, San Marcos, CA (US)

(73) Assignee: Invuity, Inc., San Francisco, CA (US)

( * ) Notice: Subject to any disclaimer, the term of this patent is extended or adjusted under 35 U.S.C. 154(b) by 0 days.

(21) Appl. No.: 11/397,446

(22) Filed: Apr. 3, 2006

(65) Prior Publication Data

US 2006/0268570 A1    Nov. 30, 2006

Related U.S. Application Data

(60) Provisional application No. 60/668,442, filed on Apr. 4, 2005, provisional application No. 60/724,717, filed on Oct. 7, 2005.

(51) Int. Cl.
*A61B 1/06*    (2006.01)
*A61B 18/18*   (2006.01)

(52) U.S. Cl. .................. 600/178; 600/114; 600/136; 600/182; 362/574; 606/14

(58) Field of Classification Search ............... 600/178, 600/179, 182, 136, 132, 114, 135, 137; 385/15; 362/574; 606/13–16
See application file for complete search history.

(56) References Cited

U.S. PATENT DOCUMENTS

| | | | | |
|---|---|---|---|---|
| 2,843,112 A * | 7/1958 | Miller | .................. | 600/178 |
| 3,261,349 A * | 7/1966 | Wallace | .................. | 600/135 |
| 3,498,286 A * | 3/1970 | Koester et al. | .................. | 600/325 |
| 3,770,342 A * | 11/1973 | Dudragne | .................. | 351/221 |
| 4,589,404 A * | 5/1986 | Barath et al. | .................. | 600/108 |
| 4,736,733 A * | 4/1988 | Adair | .................. | 600/109 |
| 4,819,620 A * | 4/1989 | Okutsu | .................. | 600/114 |
| 5,419,313 A * | 5/1995 | Lemke | .................. | 600/133 |
| 5,423,312 A * | 6/1995 | Siegmund et al. | .................. | 600/109 |
| 5,538,497 A * | 7/1996 | Hori | .................. | 600/182 |
| 5,617,498 A * | 4/1997 | Cawood | .................. | 385/117 |
| 5,947,958 A * | 9/1999 | Woodard et al. | .................. | 606/15 |
| 6,293,910 B1 * | 9/2001 | Yamakita et al. | .................. | 600/132 |
| 6,306,083 B1 * | 10/2001 | Bonne et al. | .................. | 600/182 |
| 6,350,233 B1 * | 2/2002 | Lubowski | .................. | 600/158 |
| 6,449,006 B1 * | 9/2002 | Shipp | .................. | 348/70 |
| 6,478,730 B1 * | 11/2002 | Bala et al. | .................. | 600/121 |
| 6,551,346 B2 * | 4/2003 | Crossley | .................. | 607/88 |
| 6,679,838 B2 * | 1/2004 | Bala | .................. | 600/178 |

(Continued)

*Primary Examiner*—John P Leubecker
(74) *Attorney, Agent, or Firm*—Paul J. Backofen, Esq.; Crockett & Crockett (57) ABSTRACT

The illumination system is a cannula comprising a transparent or semitransparent material capable of carrying light from the proximal end of the cannula to the distal end of the cannula, thereby illuminating a surgical field. The surgical field is thus illuminated through components that do not occupy space that may otherwise by used for optics and or surgical tools. The illumination source may be optically coupled with the cannula at any appropriate location. The cannula comprises a sterilizable polymer which functions as a waveguide. A waveguide is a material medium that confines and guides light. When in use, the light source connected to the hub provides light which may be guided to the distal end of the cannula or any other suitable location. Thus, the sheath provides structure-guided illumination resulting in the illumination of the surgical site.

7 Claims, 5 Drawing Sheets

U.S. PATENT DOCUMENTS

| | | | |
|---|---|---|---|
| 6,814,699 B2 * | 11/2004 | Ross et al. | 600/179 |
| 6,863,651 B2 * | 3/2005 | Remijan et al. | 600/130 |
| 6,871,000 B1 * | 3/2005 | Fukuba et al. | 385/143 |
| 2002/0193664 A1 * | 12/2002 | Ross et al. | 600/178 |
| 2003/0163030 A1 * | 8/2003 | Arriaga | 600/182 |
| 2006/0069314 A1 * | 3/2006 | Farr | 600/179 |
| 2006/0211918 A1 * | 9/2006 | Lieponis | 600/182 |

* cited by examiner

OPTICAL WAVEGUIDE SHEATH

RELATED APPLICATION

The present application claims priority from U.S. provisional patent application Ser. No. 60/668,442 filed Apr. 4, 2005 and U.S. provisional patent application Ser. No. 60/724,717 filed Oct. 7, 2005.

FIELD OF THE INVENTIONS

The present invention relates generally to the field of surgical illumination and more specifically to optical waveguide endoscope illumination.

BACKGROUND OF THE INVENTION

Figure 1:
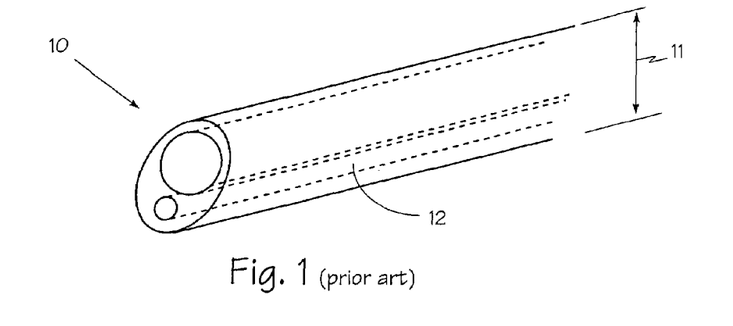
FIG. 1 is a perspective view of the distal end of a conventional endoscope.

Currently optical fiber illumination elements such as element 12 shown in FIG. 1 are used exclusively in medical illumination where small packaging is critical. Devices such as endoscope 10 are the most common devices that currently use optical fiber illumination. Due to its compact size, optical fiber is an excellent choice for rigid endoscope illumination. However, there are complications using optical fiber illumination in flexible endoscope applications.

Although the cost of raw glass or plastic fiber is relatively inexpensive, the cost of assembling the fiber into an endoscope tube may be high. Once the fiber is inserted, it generally must be glued and polished to a specific angle.

Optical fiber is extremely fragile and brittle. During the assembly process or in the field after many sterilization cycles, optical fiber may start to break down and degrade. Color change is also very common with fiber optics after many sterilization cycles. Since the fiber is integrated into endoscopes, any damage to the fiber optics also results in damage to the scope, thus causing an expensive overhaul.

A significant challenge in many endoscopic procedures is cable management. There may be many cables typically present in the sterile field; camera cable, fiber optic cable, irrigation and suction, etc. Since the optical fiber cable has the largest diameter it typically is the heaviest cable. One of the challenges that face surgeons using rigid endoscopes is constant rotation of the endoscopes to view different orientation angles. When the endoscopes are rotated, the fiber optic cable is forced to rotate around with the endoscope, thus causing interference. These issues become even more important during arthroscopic surgery. Since the optical fiber cable is heavy, it will actually rotate the endoscope, often forcing the surgeon to keep one of their hands on the fiber optic cable to prevent unwanted spinning of the endoscope.

The illumination fiber also occupies space inside an endoscope or other surgical implement. By allocating space to optical fiber illumination, the diameter of optics may be limited to maintain the smallest overall endoscope diameter.

What is needed is a multifunctional surgical illumination device.

SUMMARY

The illumination system described below comprises an arthroscope, endoscope or other suitable surgical tool and an attachable cannula or sheath comprising a transparent or semi-transparent material capable of carrying light from the proximal end of the cannula to the distal end of the cannula, thereby illuminating the surgical field. The surgical field is thus illuminated through components that do not occupy space that may otherwise by used for the optics of the arthroscope. The arthroscopic illumination system further comprises one or more illumination sources disposed at the proximal end of the cannula. The illumination source may be optically coupled with the cannula at the hub or other appropriate location. The cannula comprises a sterilizable polymer which functions as a waveguide. A waveguide is a material medium that confines and guides light. When in use, the light source connected to the hub provides light which may be guided to the distal end of the cannula or any other suitable location. Thus, the sheath provides structure-guided illumination resulting in the illumination of the surgical site.

An optical waveguide according to the present disclosure may be a single use disposable sheath that surrounds an endoscope or other suitable apparatus to conduct illumination to the distal end of the apparatus. The optical waveguide sheath may also introduce irrigation and or provide suction along the apparatus. Separating illumination from the endoscope permits increasing the aperture of endoscopes without increasing the overall dimension of the endoscope.

An optical waveguide sheath or tube according to the present disclosure provides a flexible waveguide suitable for medical applications. The optical waveguide may be separate and independent of an endoscope or other medical device and for example may be oriented coaxial to a flexible or rigid endoscope to provide light for the endoscope or other surgical device. The optical waveguide may include suitable microstructure or structures to keep the light bouncing within the waveguide independent of the outside medium or the curvature of the waveguide. The waveguide may be disposable and may be sized to accommodate an endoscope or other device within the bore, therefore the optical fiber labor component in manufacturing of endoscopes or other illuminated devices may be eliminated.

In a first aspect, the present disclosure provides a waveguide as a single unit that may be molded into custom shapes and or made single use disposable. If the waveguide is single use and sold sterile, it will be brand new for every application, so if any damage occurs during a procedure, the waveguide may be easily replaced and may be discarded after a procedure.

In another aspect of the present disclosure an optical waveguide may also operate as a cannula providing irrigation and or suction or other suitable services for medical applications.

The rotation issues previously faced with fiber optics may be resolved with an optical wave-guide because the waveguide can be designed to have a rotating ring into which the fiber optic cable is connected from a light source. Thus the waveguide can spin independently with the scope without having a need to rotate the tethered fiber cable.

In most endoscopic applications a sheath is used for suction and irrigation. This sheath fits over the endoscope. If the sheath was an optical waveguide, it may simultaneously provide suction and or irrigation as well as illumination. Since the optical fibers are eliminated from the bore of the endoscope, the optics may be manufactured to a larger diameter, thus dramatically increasing the resolution of the scope. Therefore, the overall diameter of the endoscope will not change, and the resolution will be increased.

An optical waveguide may provide illumination and at the same time perform as a surgical instrument. Other than rigid endoscopes, devices such as trocars, obturators, retractors, may all be made from waveguide material. Devices, such as laryngoscope blades can be make our of waveguide material and thus be self illuminating thus eliminating any need for fiber optics.

In another aspect of the present disclosure one or more coupling lenses may be used to couple light into an optical waveguide. The lenses or other suitable structure may adopt any suitable geometry such as for example spherical, cylindrical, aspherical and or non-symmetrical geometries. If a light source having a wide output angle such as one or more LEDs is used, a more complex lens system such as an asphere may be used to optimize light coupling.

In another aspect, one or more faces of an optical waveguide may include a predetermined micro structured pattern. Different optical light output shapes may be achieved by creating specific structured surfaces or patterns.

It is also possible to apply the structured technology to deflect light as well as focus it into a particular shape. Microstructure may be applied to the back and or the front of a refractive element to deflect the beam as well as shape it. Microstructure surfaces may also be combined with one or more air gaps and or conventional surface shaping to achieve desired optical performance.

In a still further aspect of the present disclosure one or more surfaces in an optical waveguide sheath or adapters or connectors may be polarized using any suitable technique such as micro-optic structure, thin film coating or other. Use of polarized light in a surgical environment may provide superior illumination and coupled with the use of complementary polarized coatings on viewing devices such as cameras or surgeons glasses may reduce reflected glare providing less visual distortion and more accurate color resolution of the surgical site.

A surgical illumination system according to the present disclosure may include a generally cylindrical light waveguide having a bore sized to accommodate one or more surgical instruments, an illumination source, an illumination conduit for conducting illumination energy from the illumination source, and an adapter ring for engaging the illumination conduit and coupling illumination energy from the illumination conduit to the light waveguide, the adapter ring permitting relative movement between the illumination conduit and the light waveguide.

An alternate illumination system according to the present disclosure may include an illumination source, a generally cylindrical light waveguide having a distal end and a proximal end and a bore sized to accommodate one or more instruments or tools extending from the proximal end through the distal end, the waveguide conducting illumination energy from the proximal end to the distal end and projecting the illumination energy from the proximal end, and an illumination conduit for conducting illumination energy from the illumination source to the proximal end of the light waveguide.

These and other features and advantages will become further apparent from the detailed description and accompanying figures that follow. In the figures and description, numerals indicate the various features of the disclosure, like numerals referring to like features throughout both the drawings and the description.

DETAILED DESCRIPTION OF THE INVENTIONS

The following disclosure generally refers to an optical waveguide and associated elements for conduction of light. This discussion is for example and the following disclosure may also be suitable for any electromagnetic radiation. The cross-sections illustrated are generally circular and may also adopt any suitable geometry.

Figure 2:
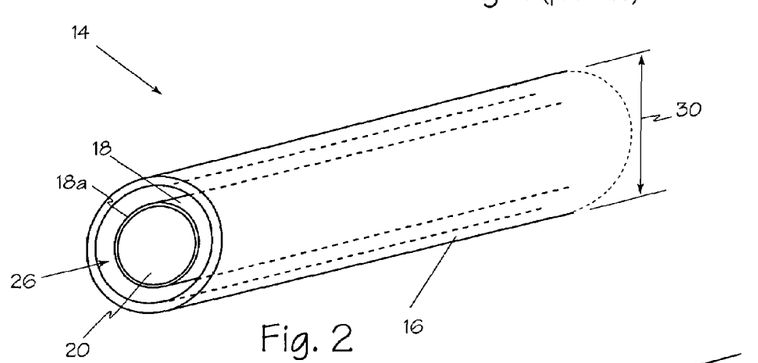
FIG. 2 is a perspective view of the distal end of an endoscope with an optical waveguide sheath according to the present disclosure.

Referring now to FIG. 2, optical waveguide system 14 may accommodate any suitable surgical instrument such as endoscope 18 which is encased, enclosed or otherwise surrounded by optical waveguide sheath 16. An optical waveguide sheath according to the present disclosure is a generally annular or cylindrical shaped structure and may be manufactured separately and may be a single use device. In the event of a failure of an optical waveguide such as optical waveguide sheath 16, a replacement may be introduced immediately. Flow path 26 is created between endoscope 18 and optical waveguide sheath 16. Flow path 26 may be used for any suitable service such as suction, irrigation or the introduction of other tools or devices.

Surgical devices such as endoscope 18 may be made without an illumination element and thus aperture 20 may be increased without increasing overall dimension 30 compared to dimension 11 of the device of FIG. 1. Wall 18A of endoscope 18 may also be perform as optical waveguide to improve illumination and may provide an alternate light path to enable illumination of different characteristics.

Figure 3:
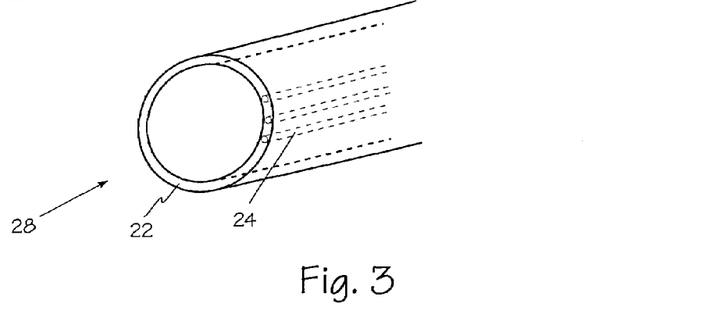
FIG. 3 is a perspective view of the distal end of an optical waveguide sheath according to the present disclosure.
Figure 14:
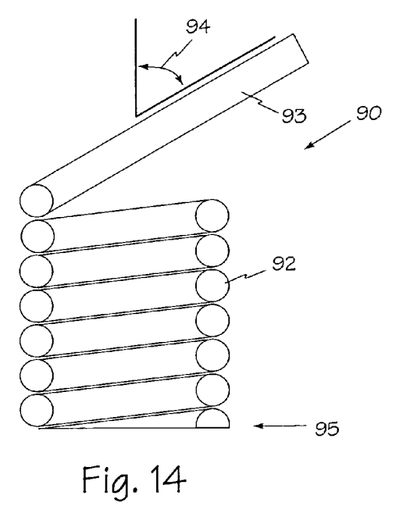
FIG. 14 is a cutaway view of an alternate optical waveguide.
Figure 14A:
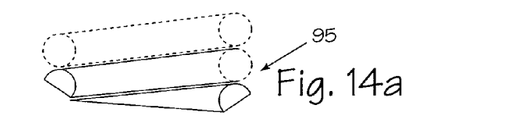
FIG. 14a-14d are cutaway views of alternate distal ends of the optical waveguide of FIG. 14.
Figure 14B:
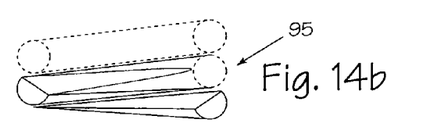
Figure 14C:
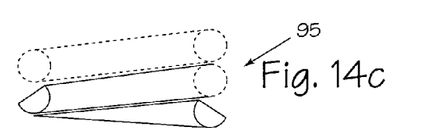
Figure 14D:
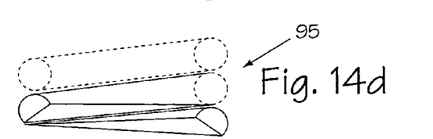

Referring now to FIG. 3, waveguide sheath 28 may be a single generally uniform element, it may be composed of two or more distinct illumination pathways forming an apparently singular conduit, or it may be composed of one or more parallel light conducting elements such as light path element 24 or light path element 92 of FIG. 14. Moving the illumination element from conventional endoscopes to a separate device such as a light conduit such as waveguide sheath 28 permits illumination surface 22 to be larger than many conventional illumination elements. Surrounding an apparatus such as an endoscope with the optical waveguide may provide generally uniform illumination for any orientation of the endoscope or other device.

Figure 4:
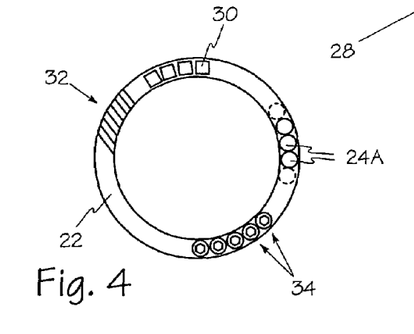
FIG. 4 is an end view of the distal end of an optical waveguide sheath according to the present disclosure.

Referring now to FIG. 4, illumination surface 22 may adopt any suitable configuration to provide illumination. For example facets such as facets 30 may direct light energy in any selected direction and may be coated or otherwise treated to introduce filtering for frequency and or polarization. Microstructures such as microstructures 32 may be used to achieve directed light energy, filtering or other. One or more lens structures may be coupled to illumination surface 22, or they may be formed in or on illumination surface such as lenses 34. Alternatively, these elements may also be combined.

Using separate light conducting elements such as light path elements 24 may permit selective illumination through a waveguide sheath as well as provide multiple illumination paths for illumination having different characteristics such as polarization, wavelength or intensity. Each light path element may include microstructures, facets, lenses or other suitable treatment on distal face 24A.

Figures 5, 6:
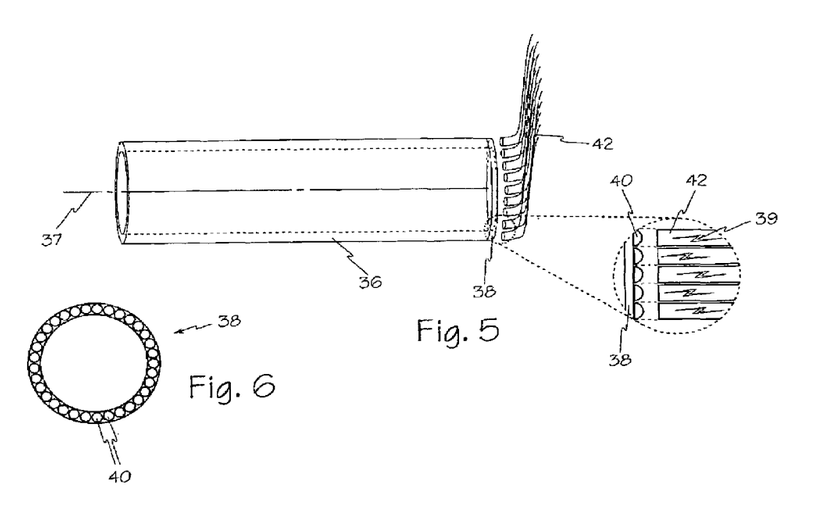
FIG. 5 is a side view of an optical waveguide sheath coupling to fiber optic elements.
FIG. 6 is an end view of the fiber optic coupling lens array of FIG. 5.

In FIGS. 5 and 6 coupling ring 38 is provided to couple light from fibers 42 into optical waveguide 36. Coupling ring 38 permits rotation of optical waveguide 36 about bore centerline 37 without rotating fibers 42. Coupling ring 38 may include any suitable light coupling structure such as coupling lenses such as lenses 40, each lens coupling light energy 39 from a fiber 42 into optical waveguide 36. The lenses or suitable microstructure may be spherical, cylindrical or aspherical or non-symmetrical depending on the light source. In the case of fiber optics, a spherical lens may be used to match the numerical apertures (acceptance angle) of the fiber optic and the optical waveguide. Because a specific cone angle of light exits a fiber optic cable, a matching acceptance angle should be used for the coupling ring.

Figure 7:
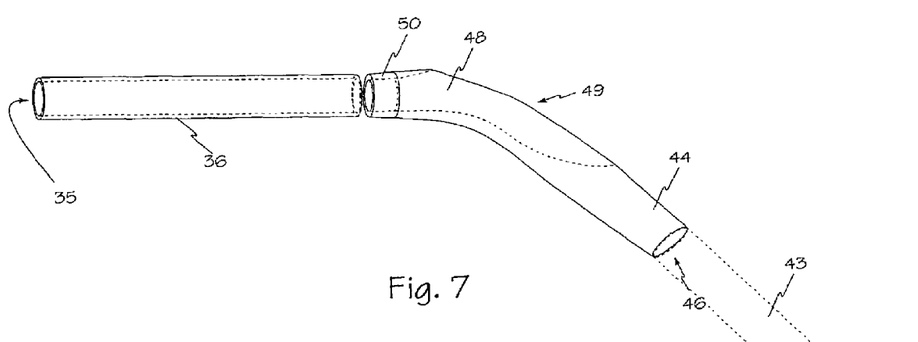
FIG. 7 is a side view of an optical waveguide sheath with a light coupling adapter according to the present disclosure.

Referring now to FIG. 7, light coupling adapter 44 may be used to couple light energy from light conduit 43 in through face 46 and directs the light energy around access channel 48 and through adapter ring 50 into optical waveguide 36. Access port 49 and access channel 48 provide access to bore 35 for any suitable surgical tool, apparatus or device. Adapter ring 50 engages waveguide 36 while permitting relative motion of waveguide 36 relative to light coupling adapter 44. Alternatively, coupling adapter 44, adapter ring 50 and optical waveguide 36 may be contiguous with no relative motion permitted. Coupling ring 50 may also be an element of waveguide 36 as well as an element of light coupling adapter 44.

Figure 8:
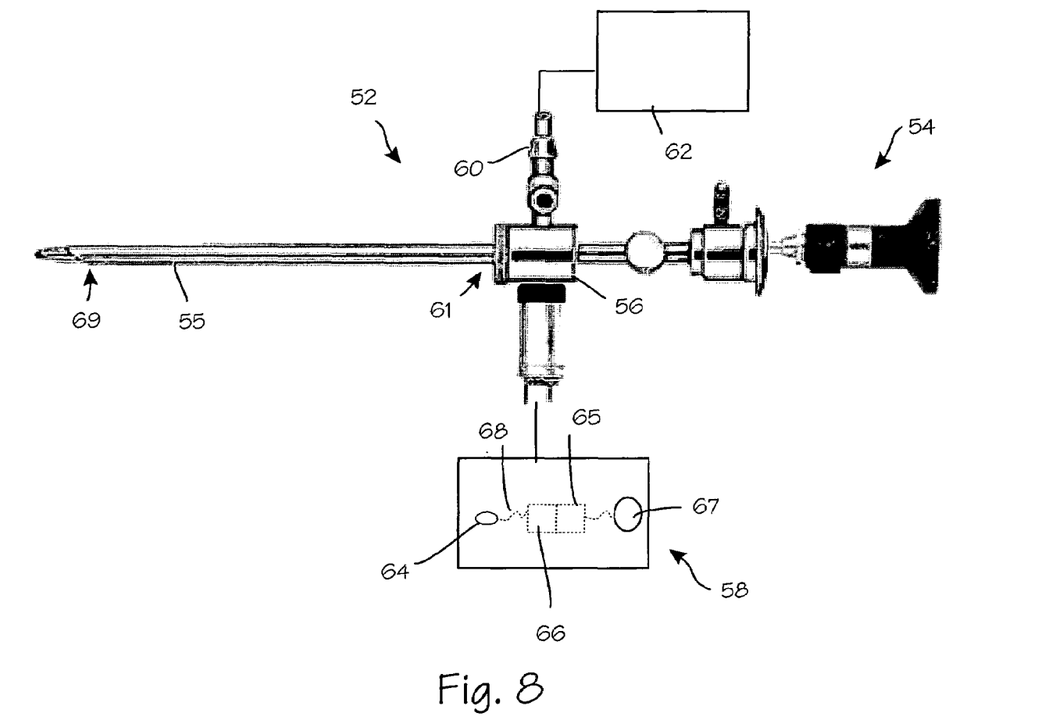
FIG. 8 is a side view of an optical waveguide illumination system with a high-resolution arthroscope disposed therein.

FIG. 8 illustrates arthroscopic illumination system 52 with a high-resolution arthroscope 54 disposed therein. The arthroscopic illumination system comprises a cannula sheath 55 adapted to provide structure-guided illumination, a hub 56 and an illumination source 58. The hub may contain one or more valves 60 and be placed in fluid communication with a vacuum and/or irrigation source 62. The cannula sheath 55 comprises a biocompatible sterilizable polymer that functions as a waveguide. The polymer may be transparent or semi-transparent and may incorporate facets, prisms, microstructures or other suitable characteristics.

An illumination source is operably coupled to the hub 56 and placed in optical communication with the cannula sheath 55. The illumination source comprises one or more LEDs 64 (light emitting diodes), a power source 66, a conductor 68 electrically connecting the power source and the LED, an LED control circuit 65 and switch 67. The LED is preferably a white-light LED, which provides a bright, white light. The power source may be provided in any form such as a power outlet or a lithium ion polymer battery. When the illumination source is illuminated, light from the illumination source propagates through the cannula sheath by means of total internal reflection, illuminating the distal end 69 of the cannula sheath. Light does not leak out of the outer diameter surface of the sleeve. The outer surfaces of the sleeve may be provided with metallic or other suitable coating to help prevent light leakage while assisting with total internal reflection. The distal end of the sleeve may be provided with a microstructure, optical component or a diffuse finish. Based on the desired optical output, a molded component or custom finish may be applied to filter or shape the light exiting the sheath.

Alternatively, the illumination source may comprise a conventional fiber light cable operably connected to the hub. The illumination source may be placed in optical communication with the sheath through optical coupling lenses disposed on the proximal end of sleeve 61 within hub 56.

Figure 9:
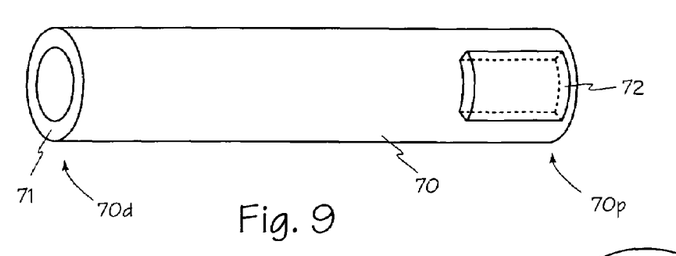
FIG. 9 is a side perspective view of an alternate optical waveguide light coupling technique.
Figure 10:
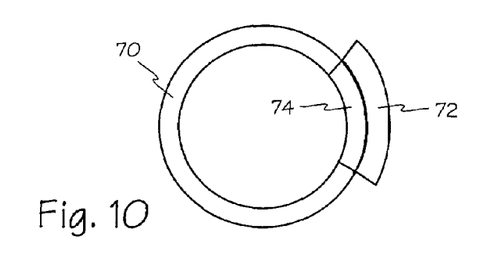
FIG. 10 is an end view of the optical waveguide of FIG. 9.

Referring now to FIGS. 9 and 10, light energy from LED array 72 may be coupled into optical waveguide 70 using reflective and or refractive optical assembly 74 in proximal end 70p such that light energy is projected from illumination surface 71 on distal end 70d.

Figure 11:
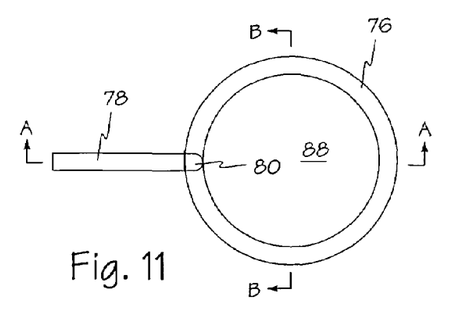
FIG. 11 is an end view of an optical waveguide with another alternate light coupling.
Figure 12:
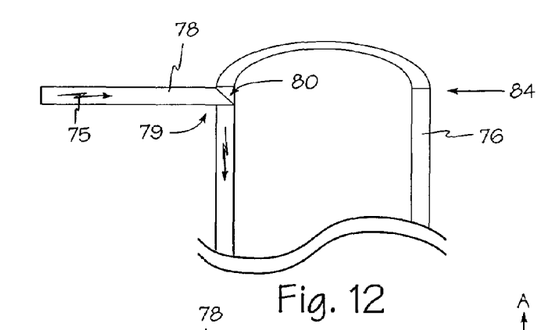
FIG. 12 is a cutaway view of the proximal end of the optical waveguide of FIG. 11 taken along A-A.
Figure 13:
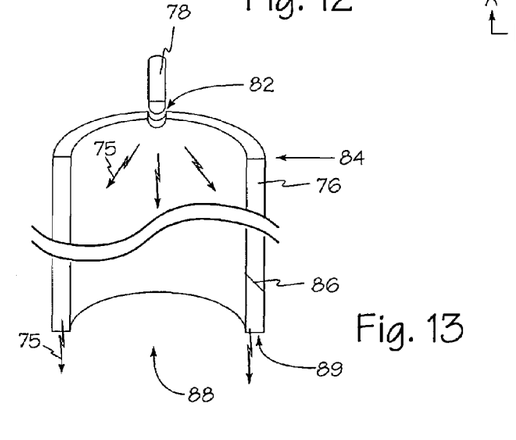
FIG. 13 is a cutaway view of the proximal end of the optical waveguide of FIG. 11 taken along B-B.

FIGS. 11, 12 and 13 illustrate an alternate light coupling into optical waveguide 76. Light 75 may be provided through any suitable conduit such as plastic rod 78. Light conduit 78 may be formed, cut or otherwise shaped at engagement end 79 to reflect light 75 at any suitable angle relative to light conduit 78. Surface 80 may include any suitable treatment, coating or microstructure to reflect a suitable amount of light 75 at a suitable angle relative to light conduit 78.

A notch, groove or other suitable indentation such as u-shaped notch 82 may be provided in proximal end 84 of an optical waveguide to engage a light conduit such as plastic rod 78. The shape of notch 82 may be selected to optimize light coupling between the light conduit and the optical waveguide. One or more structures such as facet 86 may be included in any suitable location of an optical waveguide to reflect light into bore 88 or out of the optical waveguide into areas surrounding the waveguide. Light generally exits optical waveguide through illumination surface 89.

Alternatively, optical waveguide 90 as illustrated in FIGS. 14 and 14a-14d may be formed using one or more solid light guides such as light path element or rod 92 and forming the one or more rods into a spring like spiral. Input 93 may be formed at any suitable angle 94 with an optimal angle between 45° and 90°. Distal end 95 may be cut or formed to have any suitable configuration to reflect or emit light in any suitable direction or directions as illustrated in FIGS. 14 and 14a-14d for example.

Figures 15, 16, 17A, 17B, 17C:
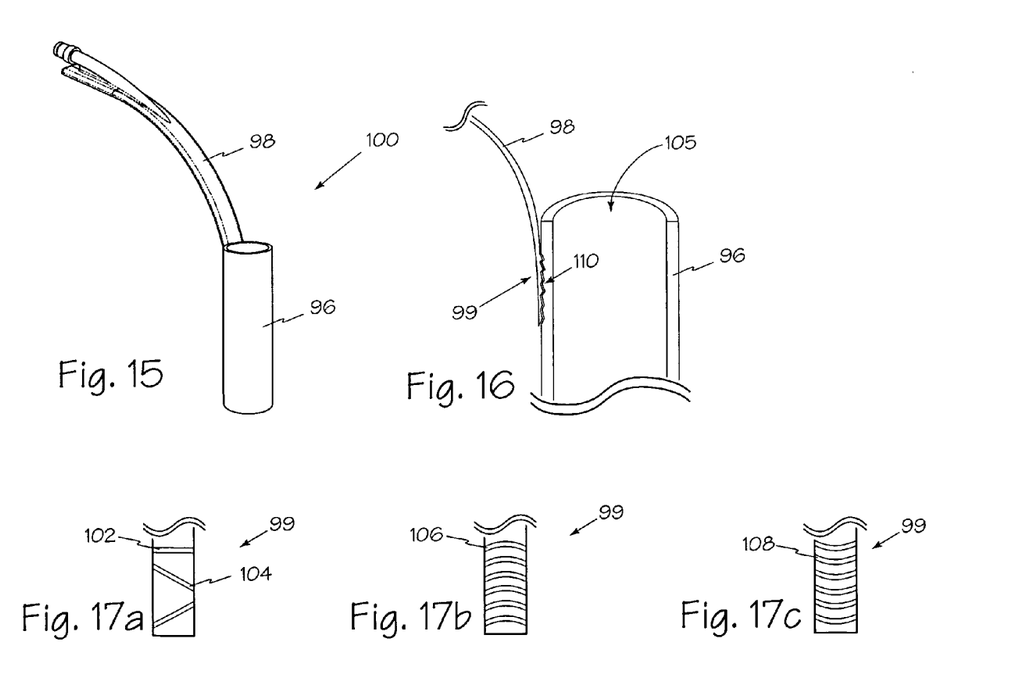
FIG. 15 is a perspective view of an optical waveguide with an alternate light coupling.
FIG. 16 is a cutaway view of the proximal end of the optical waveguide of FIG. 15.
FIG. 17a-17c are front views alternate distal ends of the light coupling of FIG. 15.

Surgical illumination system 100 may include optical waveguide 96 and light adapter 98. Distal end 99 of light adapter 98 may have any suitable shape as illustrated in FIGS. 17a-17c. Lenses or other optical structures such as lenses 102, 104, 106 and 108 may have any suitable shape or orientation to optimize light coupling or output. Different lenses may also be combined on a light adapter as in FIG. 17a. A complimentary surface 110 may be produced in optical waveguide 96 to achieve selected light transfer or coupling. Alternatively, light adapter may extend through optical waveguide 96 such that lenses such as lenses 102, 104, 106 and or 108 directly illuminate bore 105 and or the surgical site.

An optical waveguide may also be used with any suitable end cap engaging the distal end of the optical waveguide. The end cap may or may not be used to modify or reflect the illumination energy. Similarly, shims may be used within the optical waveguide to orient any tool or tools within the waveguide and the shims may or may not conduct or modify the illumination energy.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A surgical illumination system comprising:
   a generally cylindrical light waveguide formed of a homogenous uncoated material and having a bore defining an open space from a proximal end to a distal end and sized to accommodate one or more surgical instruments;
   an illumination source;
   an illumination conduit having an input and an output for conducting illumination energy from the illumination source at the input, the illumination conduit forming an obtuse angle between the input and the output; and
   an adapter ring for engaging the illumination conduit and simultaneously coupling illumination energy from the illumination conduit to the light waveguide for surgery, and permitting relative movement between the illumination conduit and the light waveguide.

2. The surgical illumination system of claim 1 wherein the light waveguide is flexible.

3. The surgical illumination system of claim 1 wherein the light waveguide is rigid.

4. The surgical illumination system of claim 1 wherein the illumination conduit is a plurality of optical fibers.

5. The surgical illumination system of claim 1 wherein the illumination conduit. further comprises an access port to accommodate the one or more surgical instruments.

6. The surgical illumination system of claim 1 wherein the illumination source comprises a plurality of LEDs.

7. The illumination system of claim 1 wherein the illumination conduit and the waveguide are formed of the same material.

* * * * *